US012678150B2

(12) United States Patent
Perszyk

(10) Patent No.: US 12,678,150 B2
(45) Date of Patent: Jul. 14, 2026

(54) OCCLUDER MEDICAL DEVICE

(71) Applicant: St. Jude Medical, Cardiology Division, Inc., St. Paul, MN (US)

(72) Inventor: Brian Perszyk, Shoreview, MN (US)

(73) Assignee: ST. JUDE MEDICAL, CARDIOLOGY DIVISION, INC., St. Paul, MN (US)

( * ) Notice: Subject to any disclaimer, the term of this patent is extended or adjusted under 35 U.S.C. 154(b) by 278 days.

(21) Appl. No.: 18/336,312

(22) Filed: Jun. 16, 2023

(65) Prior Publication Data

US 2023/0404559 A1 Dec. 21, 2023

Related U.S. Application Data

(60) Provisional application No. 63/353,436, filed on Jun. 17, 2022.

(51) Int. Cl.
*A61B 17/00* (2006.01)
(52) U.S. Cl.
CPC ...................... *A61B 17/0057* (2013.01); *A61B 2017/00526* (2013.01); *A61B 2017/00592* (2013.01); *A61B 2017/00601* (2013.01)
(58) Field of Classification Search
CPC ...... A61B 17/0057; A61B 2017/00243; A61B 2017/00526; A61B 2017/00592; A61B 2017/00597; A61B 2017/00601; A61B 2017/00606
See application file for complete search history.

(56) References Cited

U.S. PATENT DOCUMENTS

| | | | |
|---|---|---|---|
| 8,777,974 B2 | 7/2014 | Amplatz et al. | |
| 8,821,529 B2 | 9/2014 | Kariniemi et al. | |
| 10,433,851 B2 | 10/2019 | Adams | |
| 10,675,450 B2 | 6/2020 | Finch | |
| 2007/0265656 A1 | 11/2007 | Amplatz et al. | |
| 2012/0245623 A1* | 9/2012 | Kariniemi .......... | A61B 17/0057 606/213 |
| 2015/0066077 A1 | 3/2015 | Akpinar | |

(Continued)

OTHER PUBLICATIONS

European Search Report and Opinion in corresponding EP Patent Application No. 23179820.8, mailed Oct. 17, 2023, 10 pages.

(Continued)

*Primary Examiner* — Mohamed G Gabr
(74) *Attorney, Agent, or Firm* — SLEMAN & LUND LLP

(57) ABSTRACT

A medical device for treating a target site includes a body extending from a proximal end to a distal end along a central longitudinal axis, the body including a proximal disc adjacent the proximal end, a distal disc adjacent the distal end, and a waist extending between and connecting the proximal and distal discs. The body further includes an inner layer formed from a first braided self-expanding material and an outer layer formed from a second braided self-expanding material, wherein the outer layer surrounds the inner layer and is independent from the inner layer. Each of the proximal disc, the distal disc, and the waist are defined in part by each of the inner layer and the outer layer. The first braided self-expanding material includes a first number of wires and the second braided self-expanding material includes a second number of wires greater than the first number of wires.

20 Claims, 7 Drawing Sheets

(56)     References Cited

U.S. PATENT DOCUMENTS

| | | | |
|---|---|---|---|
| 2015/0073538 A1 | 3/2015 | Thomas | |
| 2019/0175339 A1 | 6/2019 | Vidlund | |
| 2021/0059651 A1* | 3/2021 | Gutfinger | ........... A61B 17/0057 |
| 2021/0059684 A1 | 3/2021 | Meyer | |
| 2021/0236138 A1 | 8/2021 | Perszyk | |
| 2021/0259670 A1 | 8/2021 | Coyle | |
| 2021/0307735 A1 | 10/2021 | Russo | |
| 2022/0183694 A1 | 6/2022 | Pan | |
| 2022/0280166 A1 | 9/2022 | Morin | |

OTHER PUBLICATIONS

Extended European Search Report in EP Application No. 23179820. 8, mailed Oct. 17, 2023, 10 pages.

* cited by examiner

OCCLUDER MEDICAL DEVICE

BACKGROUND OF THE DISCLOSURE

A. Field of Disclosure

The present disclosure relates generally to medical devices that are used in the human body. In particular, the present disclosure is directed to embodiments of an occlusion device with improved conformability. More specifically, the present disclosure is directed to an occlusion device with two layers of material to optimize flexibility while maintaining radial force, reducing device protrusion, and optimizing conformability to the surrounding tissue.

B. Background

An occluder is a medical device used to treat (e.g., occlude) tissue at a target site within the human body, such as an abnormality, a vessel, an organ, an opening, a chamber, a channel, a hole, a cavity, a lumen, or the like. For example, an occluder may be used in trans-catheter secundum atrial septal defect closures. Secundum atrial septal defects (ASDs) are common congenital heart defects that allow blood to flow between the left and right atria of the heart, thus decreasing cardiac output and increasing the workload of the heart. Occluders are generally delivered through a sheath in the femoral vein and deployed in the defect to occlude blood flow.

Some occluders, when deployed, can experience various changes to their geometry over time, which can, although rarely, cause device shifting, tissue erosion, and/or device leakage. Various solutions have been contemplated to reduce or eliminate these rare adverse events. However, it has been realized that adjusting one characteristic can have unintended consequences on other aspects of the device.

Accordingly, it would be desirable to optimize an occluder to reduce or eliminate tissue erosion, device malformation, and device leakage after deployment, while maintaining occlusive functionality and ease of use.

SUMMARY OF THE DISCLOSURE

The present disclosure generally relates to medical devices and methods of manufacturing and use thereof, including one or more physical aspects optimized to enhance deployment of the device and/or reduce or eliminate tissue erosion, device malformation, and/or device leakage after deployment thereof.

In one embodiment, the present disclosure is directed to a medical device for treating a target site. The medical device includes a body extending from a proximal end to a distal end along a central longitudinal axis, the body including a proximal disc adjacent the proximal end, a distal disc adjacent the distal end, and a waist extending between and connecting the proximal disc and the distal disc. The body also includes an inner layer formed from a first braided self-expanding material, and an outer layer formed from a second braided self-expanding material, wherein the outer layer surrounds the inner layer and is independent from the inner layer. Alternatively, at least some portion of the inner layer may be sutured to at least some portion of the outer layer. Each of the proximal disc, the distal disc, and the waist are defined in part by each of the inner layer and the outer layer. The first braided self-expanding material forming the inner layer includes a first number of wires and the second braided self-expanding material forming the outer layer includes a second number of wires greater than the first number of wires.

A diameter of the inner layer of the distal disc may be less (or significantly less) than a diameter of the outer layer of the distal disc. The diameter of the inner layer of the distal disc may extend halfway between a diameter of the waist and the diameter of the outer layer of the distal disc. The diameter of the inner layer of the distal disc may extend between $\frac{1}{10}$ and $\frac{3}{4}$ of the diameter of the outer layer of the distal disc. More preferably the inner layer of the distal disc may extend between $\frac{1}{3}$ and $\frac{1}{2}$ of the diameter of the outer layer of the distal disc. The outer layer of the distal disc may have an outer diameter that extends radially about 6 mm to 8 mm beyond an outer diameter of the waist, and the inner layer of the distal disc may have a diameter that extends about 1 mm to 6 mm (or 3 mm to 5 mm) beyond the diameter of the waist. The proximal disc may be structured similarly to the distal disc.

The inner layer may have a first softness. The outer layer may have a second softness, which may be greater than the first softness. The second softness may be such that outer layer at the distal disc or the proximal disc requires the application less than one of 0.1N, 0.2N, 0.3N of radial force for 2 mm of compression. The first softness may be such that inner layer of the distal disc or the proximal disc require the application of greater than one of 0.3N, 0.4N, 0.5N or 0.6N for 2 mm of compression. The first softness and second softness may differ such that the at least 0.1N more radial force would be required to deform the inner disc 2 mm than to deform the outer disc 2 mm. The first and/or second stiffness may be such that greater than one of 0.2N, 0.3N, 0.4N or 0.5N of radial force is required to compress the waist 2 mm. The first braided self-expanding material forming the inner layer may comprise the first number of wires having a first wire diameter. The second braided self-expanding material forming the outer layer may comprise the second number of wires having a second, smaller wire diameter. The second braided self-expanding material forming the outer layer may comprise the second number of wires having a second wire diameter less than the first wire diameter. The device may have an outer diameter of about 26 mm. The first wire diameter may be between about 0.006 inches and about 0.0065 inches (about 0.1524 mm to about 0.1651 mm). The second wire diameter may be between about 0.0035 inches and about 0.004 inches (about 0.0889 mm to about 0.1016 mm). The first wire diameter may be between 0.006 inches and 0.0065 inches (0.1524 mm to 0.1651 mm). The second wire diameter may be between 0.0035 inches and 0.004 inches (0.0889 mm to 0.1016 mm). The device may have an outer diameter of about 44 mm. In some examples, the first wire diameter may be up to 0.011 inches (0.2794 mm) and the second wire diameter may be up to 0.007 inches (0.1778 mm).

The second wire diameter may be selected to optimize the second softness of the outer layer. The first wire diameter may be selected to optimize a radial and axial strength of the inner layer. The first wire diameter may be selected to optimize at least one of a radial strength and an axial strength of the inner layer, or of a combined strength of the inner and outer layers.

An inner surface of the waist defined by the inner layer may have a first radial strength. The first radial strength may be a combined strength of the inner layer and the outer layer. An outer surface of the waist defined by the outer layer may have a second radial strength less than the first radial strength.

The outer layer may comprise a pic transition along or adjacent to the waist. The pic transition may comprise an increasing braid density of the second braided self-expanding material along or adjacent to the waist. The pic transition may comprise a decreasing helix length of the second braided self-expanding material along or adjacent to the waist.

The distal disc may comprise an outer proximal surface and the proximal disc may comprise an outer distal surface. Each of the outer proximal surface and the outer distal surface may be tapered toward the waist, such that each of the outer proximal surface and the outer distal surface may gradually decrease in diameter toward the waist. Each of the outer proximal surface and the outer distal surface may be tapered such that the distance between the discs may increase toward the waist.

The distal disc may comprise a tapered proximal outer surface that is tapered toward the waist, such that the tapered proximal outer surface gradually decreases in diameter toward the waist. The distal disc may comprise a flat proximal outer surface. The distal disc may comprise an outer proximal surface that is substantially flat.

The distal disc may comprise an outer proximal surface having a concavity facing the proximal disc, such that a distance between the outer proximal surface and an outer distal surface of the proximal disc may increase from an outer edge of the distal disc to an interface of the distal disc and the waist. The distal disc may comprise a concave tapered proximal outer surface with a concavity facing the proximal disc, such that a distance between the tapered proximal outer surface and a distal outer surface of the proximal disc increases from an outer edge of the distal disc to an interface of the distal disc and the waist. The occlusive patch material may be positioned within at least one of the distal disc and the proximal disc between the outer layer and the inner layer. The occlusive patch material may be positioned within each of the distal disc, the proximal disc, and the waist between the outer layer and the inner layer. The medical device may further comprise an occlusive patch material positioned between the outer layer and the inner layer. The occlusive patch material may be positioned within the distal disc between the outer layer and the inner layer. Alternatively, the occlusive patch material may be positioned within the proximal disc between the outer layer and the inner layer. The occlusive patch material may include mending yarn.

A peripheral surface of the outer layer of the distal disc may have a rounded shape or profile. A peripheral surface of the inner layer of the distal disc may have a rounded shape or profile.

Another aspect of the present disclosure is directed to a medical device for treating a target site. The medical device includes a body extending from a proximal end to a distal end, the body including a proximal disc, a distal disc, and a waist extending between and connecting the proximal disc and the distal disc. The body also includes an inner layer and an outer layer, wherein the outer layer surrounds the inner layer. Each of the proximal disc, the distal disc, and the waist are defined in part by each of the inner layer and the outer layer. At least a portion of the inner layer may have a first one or more characteristics and at least a portion of the outer layer may have a second one or more characteristics that are different to the first one or more characteristics.

The inner layer and outer layer each may be formed from material. Each material may be a braided material. Each material may be a self-expanding material, such as a shape memory material. The material of the inner layer may be independent from the material of the outer layer. Alternatively, at least a portion of the material of the inner layer may be sutured to at least a portion of the material of the outer layer. At least a portion of the material of the inner layer may be different from at least a portion of the material of the outer layer.

The one or more characteristics of the respective layers may include a wire count, a wire diameter, and/or a braid pattern. The one or more characteristics of the respective layers may include a softness of said layer. The material forming the inner layer may comprise a first number of wires and the material forming the outer layer may comprise a second, greater number of wires than the first number of wires. The material forming the inner layer may comprise one or more wires having a first wire diameter, and the material forming the outer layer may comprise one or more wires having a second, smaller wire diameter than the first diameter. In examples in which the one or more wires of the inner layer has a larger diameter than the one or more wires of the outer layer, the number of wires in the inner layer may be the same or less than the number of wires in the outer layer. In examples in which the one or more wires of the inner layer has a smaller diameter than the one or more wires of the outer layer, the number of wires in the inner layer may be the same or less than the number of wires in the outer layer. The material forming the inner layer may be a braided material and the material forming the outer layer may be a braided material with a different braid pattern to the material forming the inner layer.

The outer layer of the discs may be more deformable than the inner layer of the discs. The outer layer of the discs may have less radial strength than the inner layer of the discs.

The first and second one or more characteristics may be selected such that the inner layer has a greater radial stiffness than the outer layer and/or the combined inner and outer layers have a greater radial stiffness than the outer layer. The first and second one or more characteristics may be selected such that the material of the inner layer has a greater stiffness than material of the outer layer. The first one or more characteristics may be selected to optimize a radial strength of the inner layer and the second one or more characteristics may be selected to optimize a softness of the outer layer.

In one aspect, a device of the present disclosure may be evaluated against the Amplatzer™ Septal Occluder ("ASO"). The ASO is a single-layer braided Nitinol mesh device, and comprises a distal disc, a proximal disc, and a waist therebetween. There is a patch interior to the proximal disc, a patch interior to the distal disc, as well as a patch and mending yarn in the waist. When testing waist compression of the ASO, measures ranging from about 0.1N to about 0.4N were obtained, with preferable ranges between 0.2N and 0.3N. Disc compression measurements of the ASO ranged from about 0.25N to about 0.8N.

A device of the disclosure includes a body extending from a proximal end to a distal end along a central longitudinal axis, the body including a proximal disc, a distal disc, and a waist extending between and connecting the proximal disc and distal disc. The body also includes an inner layer formed from a first self-expanding braided material, and an outer layer formed from a second braided self-expanding material, wherein the outer layer surrounds the inner layer and is independent from the inner layer. Each of the proximal disc, the distal disc, and the waist are defined in part by each of the inner layer and the outer layer. The first braided self-expanding material forming the inner layer has a first number of wires and the second braided self-expanding material forming the outer layer has a second, greater number of wires. When conducting a disc-edge compression test of a device of the disclosure, measures ranged from about 0.2N to about 0.35N, and preferably from about 0.25N to about 0.3N. Waist compression measure for a device of the disclosure ranged from about 0.1N to about 0.3N. Whereas the ASO disc compression test values ranged from about 0.25N to 0.8N, the disc compression test of a device of the disclosure ranged from about 0.2N to about 0.35N, thus the outer layer of the discs (either the distal disc or the proximal disc) of a device of the disclosure is softer, that is to say, more conformable, than the discs of the ASO. The radial force of the combined inner and outer layers at the waist of a device of the disclosure is equivalent to ASO strength, facilitated by adjusting the diameter of the wires used in the inner layer of the waist. The inner layer of the waist may be used to optimize the combined radial strength of the inner and outer layers of the waist. The inner layer provides some axial strength in the inner portion of a disc and the center of the device, otherwise the outer layer of the disc may be prone to more deformation. In addition, the inner layer increases the clamping force on the tissue of the atrial septum when the device is implanted, which may increase occlusion of the defect and/or minimize leak around the device.

In another embodiment, the present disclosure is directed to a method of forming a medical device. The method includes selecting a first braided self-expanding material for forming an inner layer of the medical device. This selecting includes selecting at least one of a wire count, a wire diameter, and a braid pattern of the first braided self-expanding material to optimize a radial strength of the inner layer formed using the first braided self-expanding material. The method also includes selecting a second braided self-expanding material for forming an outer layer of the medical device. This selecting includes selecting at least one of a wire count, a wire diameter, and a braid pattern of the second braided self-expanding material to optimize a softness of the outer layer formed using the second braided self-expanding material. The method further includes enclosing the first braided self-expanding material within the second braided self-expanding material, and forming the inner layer and the outer layer of the medical device by heat-setting (molding) the first and second braided self-expanding materials. Once formed, the inner layer includes an inner distal disc, an inner waist, and an inner proximal disc, and the outer layer includes an outer distal disc, an outer waist, and an outer proximal disc.

Said forming the inner layer and outer layer may comprise forming the inner distal disc to be smaller (or significantly smaller) than the outer distal disc.

The method may further comprise positioning an occlusive patch material between the inner layer and the outer layer. The method may comprise coupling the occlusive patch material to at least one of the inner layer and the outer layer.

Said selecting the second braided self-expanding material may comprise selecting the second braided self-expanding material having a pic transition at a location corresponding to the outer waist when the outer layer is formed from the second braided self-expanding material. Said selecting the second braided self-expanding material may comprise selecting a pic transition at a location along or adjacent to the outer waist when the outer layer is formed using the second braided self-expanding material.

In another aspect, the present disclosure is directed to a medical device for treating a target site. The medical device includes a body extending from a proximal end to a distal end along a central longitudinal axis, the body including a proximal disc adjacent the proximal end, a distal disc adjacent the distal end, and a waist extending between and connecting the proximal disc and the distal disc. The body further includes an inner layer formed from a first braided self-expanding material and an outer layer formed from a second braided self-expanding material, wherein the outer layer surrounds the inner layer and is independent from the inner layer, wherein each of the proximal disc, the distal disc, and the waist are defined in part by each of the inner layer and the outer layer, and wherein the first braided self-expanding material forming the inner layer includes a first number of wires and the second braided self-expanding material forming the outer layer includes a second number of wires greater than the first number of wires.

In another aspect, the present disclosure is directed to a method of forming a medical device. The method includes selecting a first braided self-expanding material for forming an inner layer of the medical device, said selecting including selecting at least one of a wire count, a wire diameter, and a braid pattern of the first braided self-expanding material to optimize a radial strength of the inner layer formed using the first braided self-expanding material. The method also includes selecting a second braided self-expanding material for forming an outer layer of the medical device, said selecting including selecting at least one of a wire count, a wire diameter, and a braid pattern of the second braided self-expanding material to optimize a softness of the outer layer formed using the second braided self-expanding material, as well as to optimize deliverability (due to the distal disc shape as the disc exits the delivery catheter) and conformability to accommodate varying anatomy with the pic transition. The method further includes enclosing the first braided self-expanding material within the second braided self-expanding material and forming the inner layer and the outer layer of the medical device by molding (heat-setting) the first and second braided self-expanding materials, the inner layer including an inner distal disc, an inner waist, and an inner proximal disc, and the outer layer including an outer distal disc, an outer waist, and an outer proximal disc.

A feature described in relation to an aspect of the disclosure above or one of the described embodiments below may be provided in combination with any other aspects or embodiments.

BRIEF DESCRIPTION OF THE DRAWINGS

Corresponding reference characters indicate corresponding parts throughout the several views of the drawings. It is understood that that Figures are not necessarily to scale.

DETAILED DESCRIPTION OF THE DISCLOSURE

Figure 1:
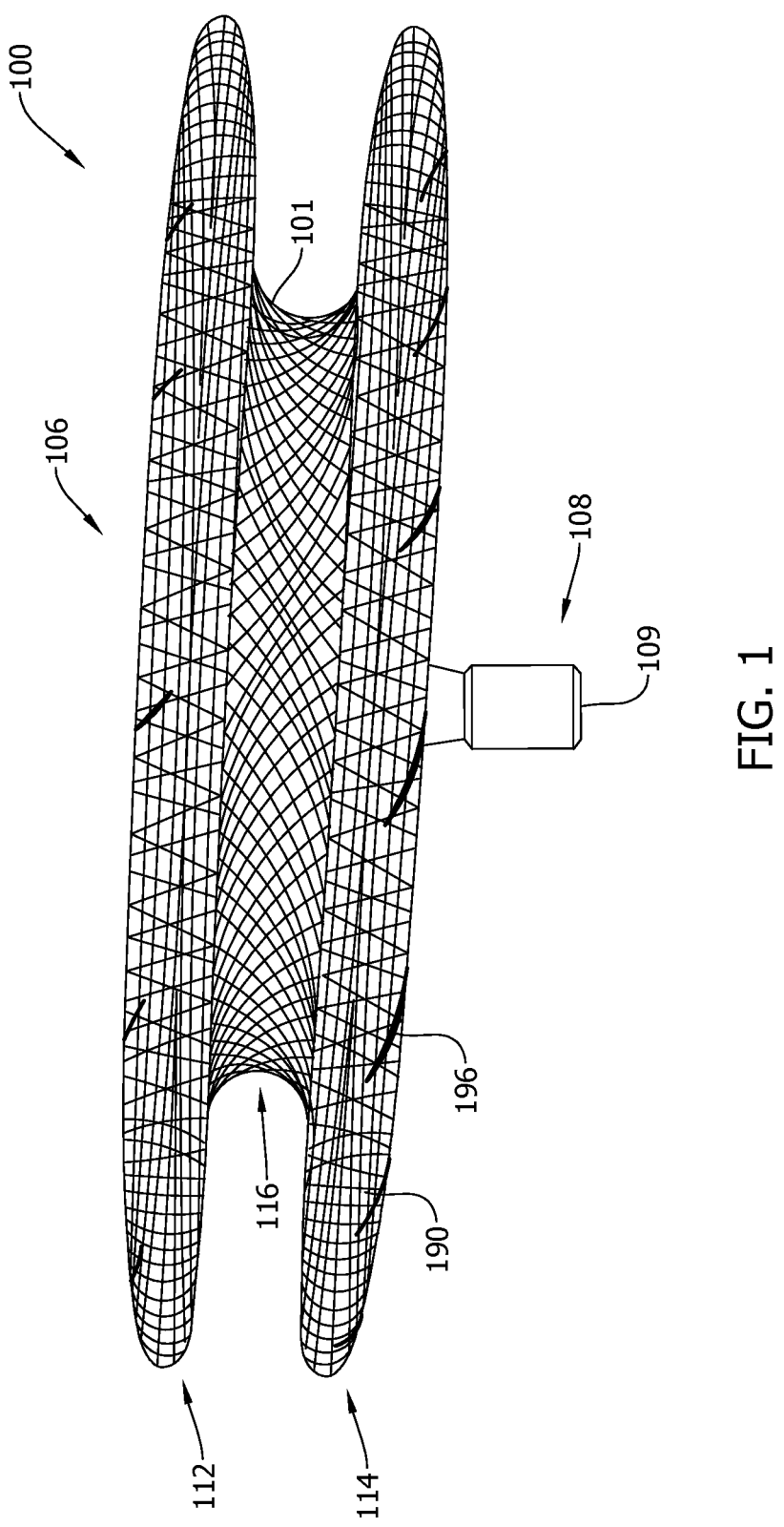
FIG. 1 illustrates an exemplary embodiment of a medical device for occluding a tissue defect in a deployed configuration, in accordance with the present disclosure.

The present disclosure relates generally to medical devices that are used in the human body. Specifically, the present disclosure relates to reducing and/or eliminating tissue erosion, device malformation, and/or device leakage associated with deployed occlusion devices. The present disclosure provides medical devices, such as occlusion devices (also referred to as "occluders"), that accomplish this objective through, for example, optimizing physical aspects of the occlusion device to improve conformability of the device with surrounding tissue.

The disclosed embodiments may lead to more consistent and improved patient outcomes. It is contemplated, however, that the described features and methods of the present disclosure as described herein may be incorporated into any number of systems as would be appreciated by one of ordinary skill in the art based on the disclosure herein.

It is understood that the use of the term "target site" is not meant to be limiting, as the medical device may be configured to treat any target site, such as an abnormality, a vessel, an organ, an opening, a chamber, a channel, a hole, a cavity, or the like, located anywhere in the body. The term "vascular abnormality," as used herein, is not meant to be limiting, as the medical device may be configured to bridge or otherwise support a variety of vascular abnormalities. For example, the vascular abnormality could be any abnormality that affects the shape of the native lumen, such as an atrial septal defect (ASD), a left atrial appendage (LAA), a lesion, a vessel dissection, or a tumor. Embodiments of the medical device may be useful, for example, for occluding an ASD, a ventricular septal defect (VSD), a patent ductus arteriosus (PDA), or a LAA as noted above. Furthermore, the term "lumen" is also not meant to be limiting, as the vascular abnormality may reside in a variety of locations within the vasculature, such as a vessel, an artery, a vein, a passageway, an organ, a cavity, or the like. For ease of explanation, the examples used herein refer to the occlusion of a septal defect (e.g., an ASD).

The term "wire," as used herein, is not meant to be limiting, as the braided self-expanding material forming the layers of material of the medical device may be formed from wires, threads, or filaments.

As used herein, the term "proximal" refers to a part of the medical device or the delivery device that is closest to the operator, and the term "distal" refers to a part of the medical device or the delivery device that is farther from the operator at any given time as the medical device is being delivered through the delivery device. In addition, the terms "deployed" and "implanted" may be used interchangeably herein.

Some embodiments of the present disclosure provide an improved percutaneous catheter directed intravascular occlusion device for use in the vasculature in patients' bodies, such as blood vessels, channels, lumens, a hole or holes through tissue, cavities, and the like, such as an atrial septal defect. Other physiologic conditions in the body occur where it is also desirous to occlude a vessel or other passageway to prevent blood flow into or therethrough. These device embodiments may be used anywhere in the vasculature where the anatomical conditions are appropriate for the design.

The medical device may include a braided device body having proximal and distal discs, where the braided material acts as an occlusive material, which is configured to substantially preclude or occlude the flow of blood. As used herein, "substantially preclude or occlude flow" shall mean, functionally, that blood flow may occur for a short time, but that the body's tissue growth to the cover (or medical device) results in occlusion or flow stoppage after this initial time period. In some embodiments, the medical device further includes one or more patches (e.g., fabric patches, bioabsorbable or bioresorbable patches, etc.) to enhance the occlusive effects of and/or tissue ingrowth along the medical device.

The present disclosure now will be described more fully hereinafter with reference to the accompanying drawings, in which some, but not all, embodiments of the disclosure are shown. Indeed, this disclosure may be embodied in many different forms and should not be construed as limited to the embodiments set forth herein; rather, these embodiments are provided so that this disclosure will satisfy applicable legal requirements. Like numbers refer to like elements throughout.

Figure 2:
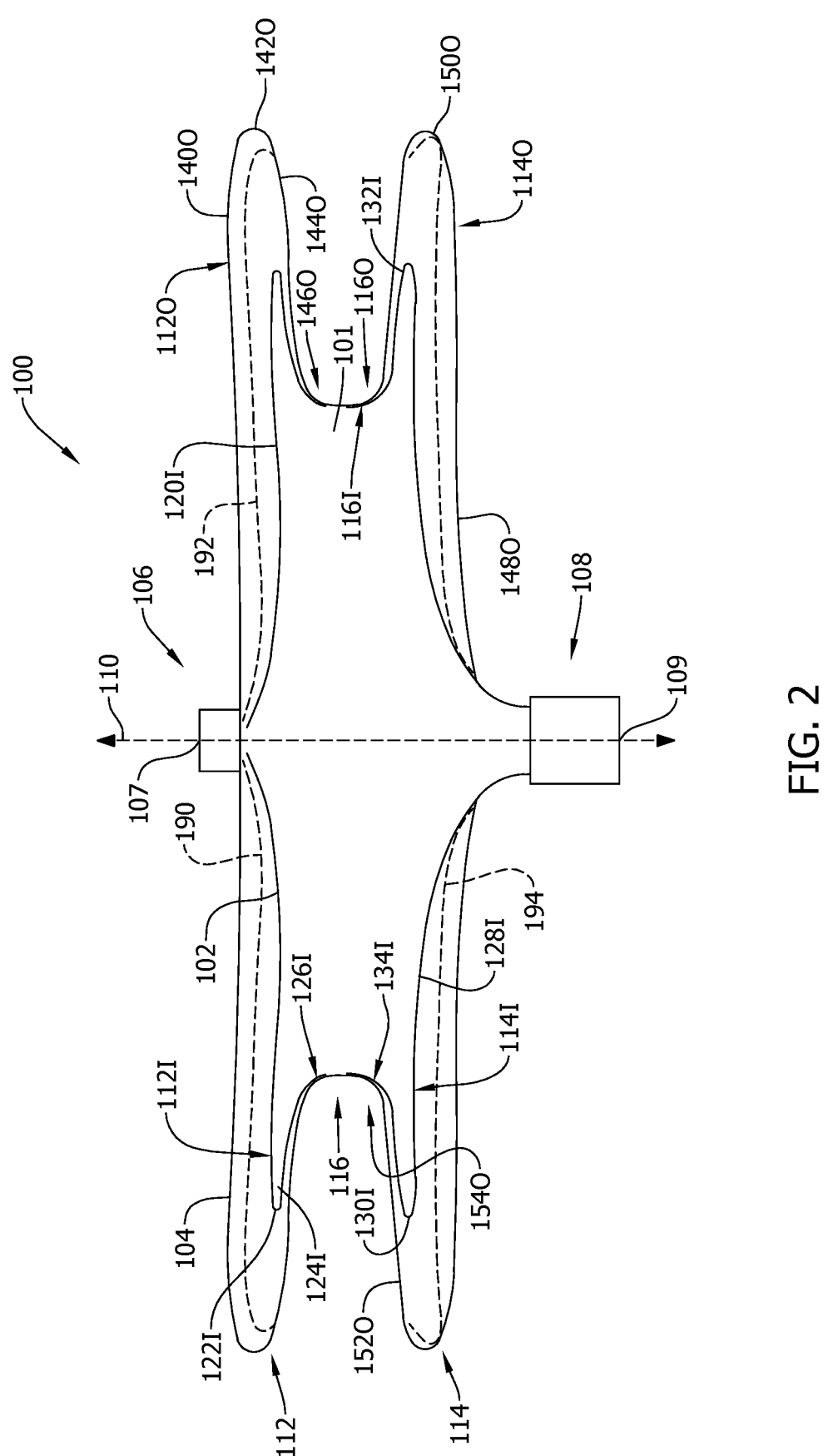
FIG. 2 illustrates a cross-sectional view of the medical device shown in FIG. 1.

Turning now to the figures, FIGS. 1 and 2 illustrate one embodiment of a medical device 100—also referred to herein as an occlusive medical device or occluder—in accordance with the present disclosure. In particular, as described further herein, medical device 100 is a dual-layer device, having an inner layer optimized to maximize radial strength and/or axial strength of medical device 100, and an outer layer optimized for softness, flexibility, and/or conformance to surrounding tissue when medical device 100 is deployed at a target site. It has been recognized that the optimized characteristics, as described further herein, may have a substantial impact on the reliability and usability of the final formed medical device. In one particular embodiment, medical device 100 is configured to be deployed within and occlude an ASD, although it is contemplated that medical device 100 may be configured to occlude other tissue defects.

As used herein, "softness" refers generally to a deformability of a material or structure. The softer a material is, the more readily it will deform when engaged with adjacent tissue. Softness may, in some instances, be contrasted with "stiffness", which refers generally to a resistance to deformation. The stiffer a material or structure is, the more it will resist deformation when engaged with adjacent tissue. Accordingly, where a "softness" of the outer layer is contrasted with a "stiffness" ("less softness") of the inner layer, this description may refer generally to an increased deformability of the outer layer as compared to a decreased deformability of the inner layer. For instance, due to the dual layer construction of the medical device(s) disclosed herein, the inner layer provides stiffness—and, therefore, support—in areas of the device where deformation is undesirable (e.g., a center of the device axially into the atria, and the waist of the device) due to the need for occlusion. This advantage is realized without limiting deformability of the outer layer in areas of the device where deformation is more desirable (e.g., the outer edges of the disc(s)), to limit impact on tissue and potential for erosion.

The softness, deformability, or axial or radial stiffness of a structure such as a portion of a medical device may be measured by compression testing using techniques known in the art. In some aspects of the present disclosure, the softness of the outer discs and that of the combined structure provided by the inner and outer portions of the waist are of particular interest.

The discs can be compression tested by inserting the medical device into a simulated defect and compressing an edge of a disc in a radial direction of the disc by applying a compressive force to an edge of the disc using a plate push. The compression test may deform a disc up to 4 mm, but preferably up to 2 mm. The force used to achieve the deformation is measured to provide a relative measure of softness of the outer layer of the disc, which depends on the used material and structure. An outer layer of a disc that is relatively soft compared to an inner layer, or as compared to the combined stiffness of the inner and outer discs, of the same disc may undergo a compression of 2 mm on application of lesser radial force than would be required to deform the inner layer of the disc when tested alone, or in combination with the outer layer, by the same distance. The softness of the inner layer of a disc may also be assessed indirectly for a device because the stiffness of the disc is proportional to the stiffness of the waist of the device. The combined stiffness of the inner and outer layers of the waist can be determined using a similar technique of applying a compressive radial force to the waist structure by placing the waist between two plates and determining the force required for a particular radial compression. The discs are positioned on either side of the plates in such a set-up.

Figure 4:
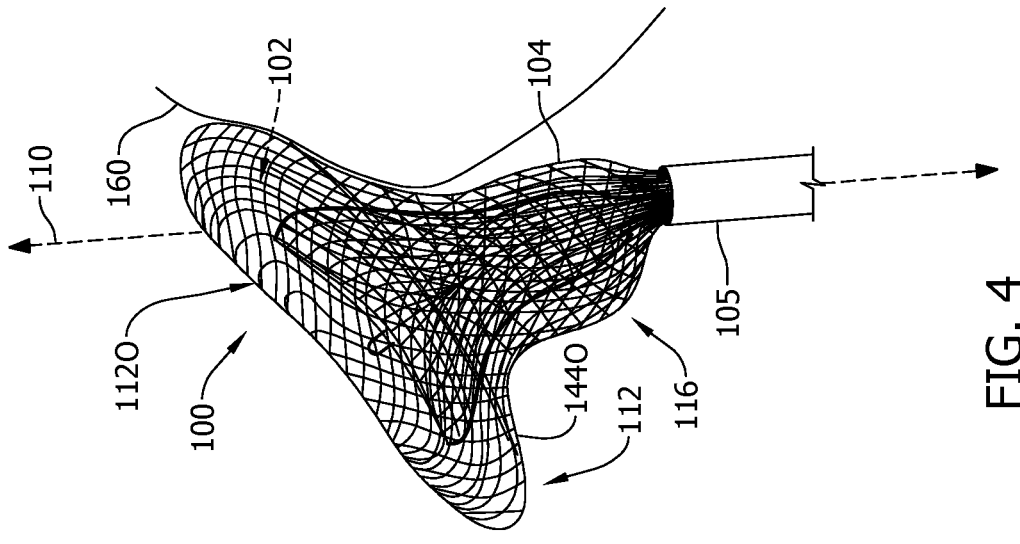
FIG. 4 illustrates an exemplary embodiment of a medical device in accordance with the present disclosure, during deployment relative to example tissue.
Figure 3:
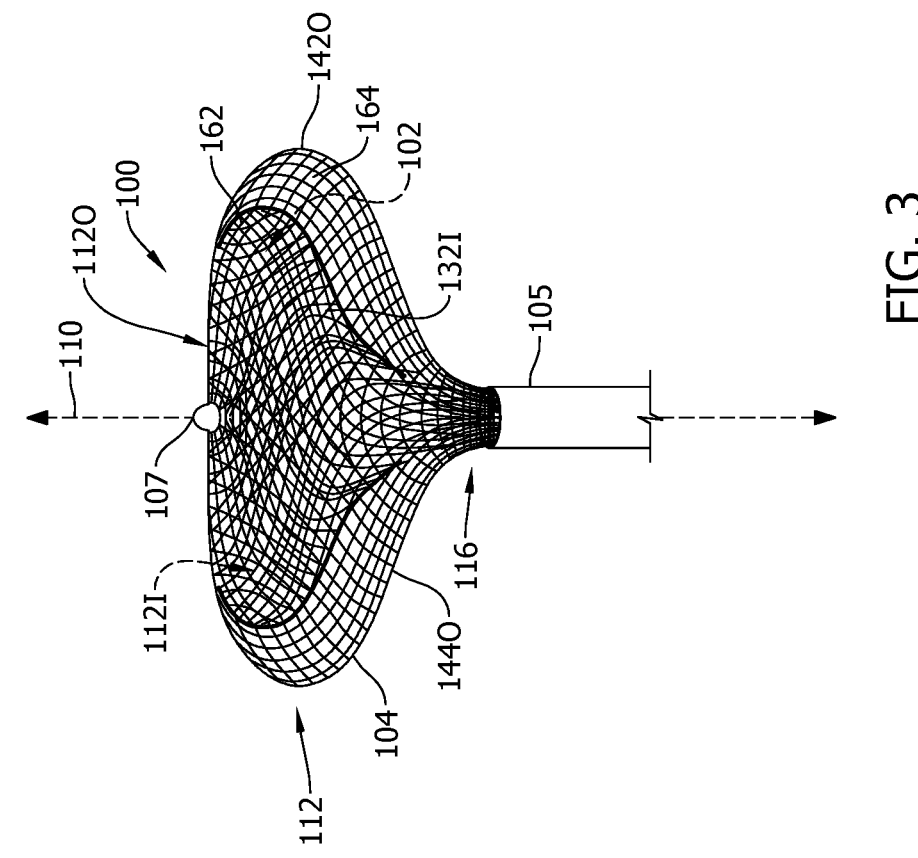
FIG. 3 illustrates an exemplary embodiment of a medical device in accordance with the present disclosure, during deployment thereof.

With reference both to the side view of FIG. 1 and the cross-sectional view of FIG. 2, medical device 100 includes a device body 101 formed from a first or inner layer 102 of braided self-expanding material and a second or outer layer 104 of braided self-expanding material. As described further herein, although each of the inner and outer layers 102, 104 may be formed from a similar source or type of material, such as Nitinol, the characteristics of inner layer 102 differ significantly from the characteristics of outer layer 104. In this way, the material forming inner layer 102 is described as a "different material" from that of the material forming the outer layer 104. For example, the materials forming inner and outer layers 102, 104 could be the same (e.g., the same chemical composition) but still described as different materials due to differences in structure, wire diameter, and/or wire number. FIGS. 1-5 illustrate medical device 100 in various stages of deployment, such as from a delivery catheter 105 (shown in FIGS. 3 and 4). Medical device 100 may be navigated to the target site for deployment using delivery catheter 105 (see FIGS. 3 and 4). For example, delivery catheter 105 may be introduced to the patient's body via transfemoral insertion or any other suitable method. Medical device 100 is constricted within delivery catheter 120 in a collapsed or contracted delivery configuration. Once at the target site, medical device 100 is advanced from a distal end of delivery catheter 105, as shown in FIGS. 3 and 4. Once deployed from delivery catheter 105, medical device 100 expands to an expanded, installation configuration, as shown in FIG. 1.

Medical device 100 extends from a distal end 106 to a proximal end 108 along a central longitudinal axis 110. Distal end 106 is used interchangeably herein to refer to a distal end of medical device 100 more generally, and a distal end of device body 101 more specifically. Likewise, proximal end 108 is used interchangeable herein to refer to a proximal end of medical device 100 more generally, and a proximal end of device body 101 more specifically.

Device body 101 includes a distal disc 112 adjacent the distal end 106 and a proximal disc 114 adjacent the proximal end 108. A waist 116 extends between and connects distal disc 112 and proximal disc 114. When medical device 100 is deployed to occlude an ASD, distal disc 112 is seated in the left atrium, and therefore may sometimes be referred to as a "left" disc. Likewise, when medical device 100 is deployed to occlude an ASD, proximal disc 114 is seated in the right atrium, and therefore may sometimes be referred to as a "right" disc.

Each of distal disc 112, proximal disc 114, and waist 116 is defined in part by both of inner layer 102 and outer layer 104. That is, distal disc 112 is defined in part by inner layer 102 (e.g., an inner distal disc 112I) and in part by outer layer 104 (e.g., an outer distal disc 112O), proximal disc 114 is defined in part by inner layer 102 (e.g., an inner proximal disc 114I) and in part by outer layer 104 (e.g., an outer proximal disc 114O), and waist 116 is defined in part by inner layer 102 (e.g., an inner waist 116I) and in part by outer layer 104 (e.g., an outer waist 116O). In this way, features of inner distal disc 112I, inner proximal disc 114I, and inner waist 116I—that is, features of inner layer 102— are referred to as "inner" features and may in some instances be denoted with a suffix "I", for the sake of clarity in the present disclosure. Similarly, features of outer distal disc 112O, outer proximal disc 114O, and outer waist 116O—that is, features of outer layer 104—are referred to as "outer" features and may in some instances be denoted with a suffix "O".

In the illustrated embodiment, inner distal disc 112I includes an inner distal surface 120I, an inner peripheral surface 122I, and an inner proximal surface 124I. In one exemplary embodiment, inner peripheral surface 122I is a relatively thin interface between inner distal surface 120I and inner proximal surface 124I, such that inner distal disc 112I is substantially flat. In some embodiments, inner peripheral surface 122I may have a rounded shape or profile. Inner proximal surface 124I is substantially planar and connects to inner waist 116I at an inner distal interface 126I. It is contemplated that in one or more alternative embodiments, inner proximal surface 124I may be tapered inwardly, to accommodate thicker tissue (see, for example, FIG. 6) or may be tapered outwardly, to accommodate thinner tissue (see, for example, FIGS. 7A and 7B).

In the illustrated embodiment, inner proximal disc 114I includes an inner proximal surface 128I, an inner peripheral surface 130I, and an inner distal surface 132I. Inner distal surface 132I connects to inner waist 116I at an inner proximal interface 134I.

Figure 6:
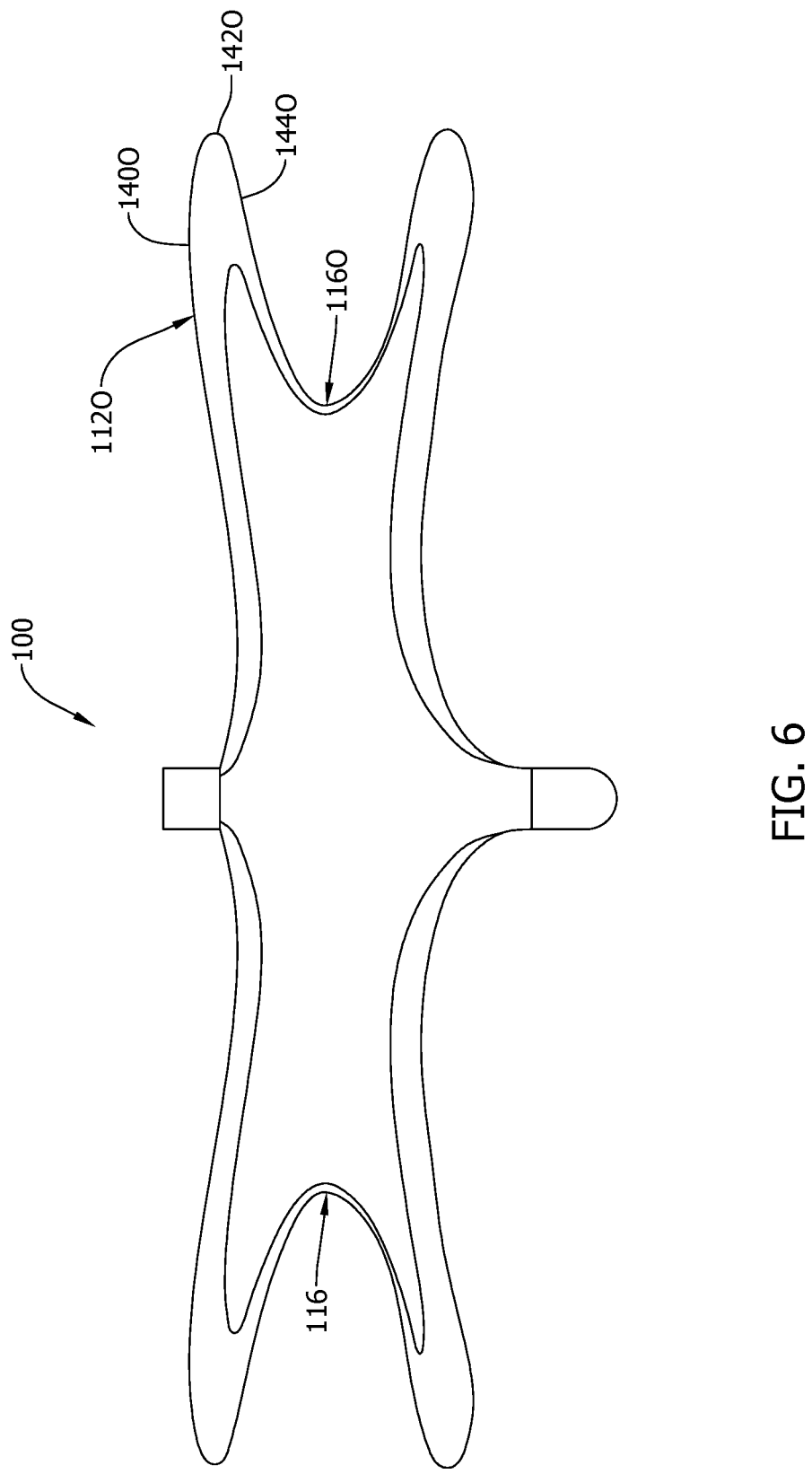
FIG. 6 illustrates a side cross-sectional view of another exemplary embodiment of a medical device in accordance with the present disclosure.

Outer distal disc 112O includes an outer distal surface 140O, an outer peripheral surface 142O, and an outer proximal surface 144O. In one exemplary embodiment, outer peripheral surface 142O is a relatively thin interface between outer distal surface 140O and outer proximal surface 144O, and may have a slightly rounded or atraumatic shape or profile. In one embodiment, as shown in FIG. 2, for example, outer proximal surface 144O is substantially flat or planar. In other embodiments, as shown in FIG. 6, for example, outer proximal surface 144O tapers radially inwardly (e.g., decreases in diameter) gradually from outer peripheral surface 142O, proximally towards outer waist 116O. Outer proximal surface 144O connects to outer waist 116O at an outer distal interface 146O.

In the illustrated embodiment, outer proximal disc 114O includes an outer proximal surface 148O, an outer peripheral surface 150O, and an outer distal surface 152O. Outer distal surface 152O connects to outer waist 116O at an outer proximal interface 154O.

It has been discerned in the conception of the present disclosure that forming distal disc 112 with a relatively flat outer proximal surface 144O, as shown in FIGS. 1 and 2 (or, in some instances, distal disc 112 with a tapered outer proximal surface 144O, as shown in FIG. 6), facilitates ensuring that distal disc 112 deflects more reliably around the aorta (or other tissue), thereby distributing the force applied by distal disc 112 (and proximal disc 114) over a greater surface area of tissue. Moreover, in embodiments in which the outer proximal surface 144O has an inwardly tapering shape, as shown in FIG. 6, there may exist an advantageous reduction in bulging of distal disc 112 into the atrium when medical device 100 is deployed (compared to at least some previous designs of an ASD occluder). Still further, it has been discovered that forming the outer proximal surface 144O to have a flat or inwardly tapering shape can improve the ability of distal disc 112 to better conform to the tissue and, therefore, to seat more reliably in the tissue defect during deployment thereof, as described further herein (see, for example, FIG. 4).

Figures 7A, 7B:
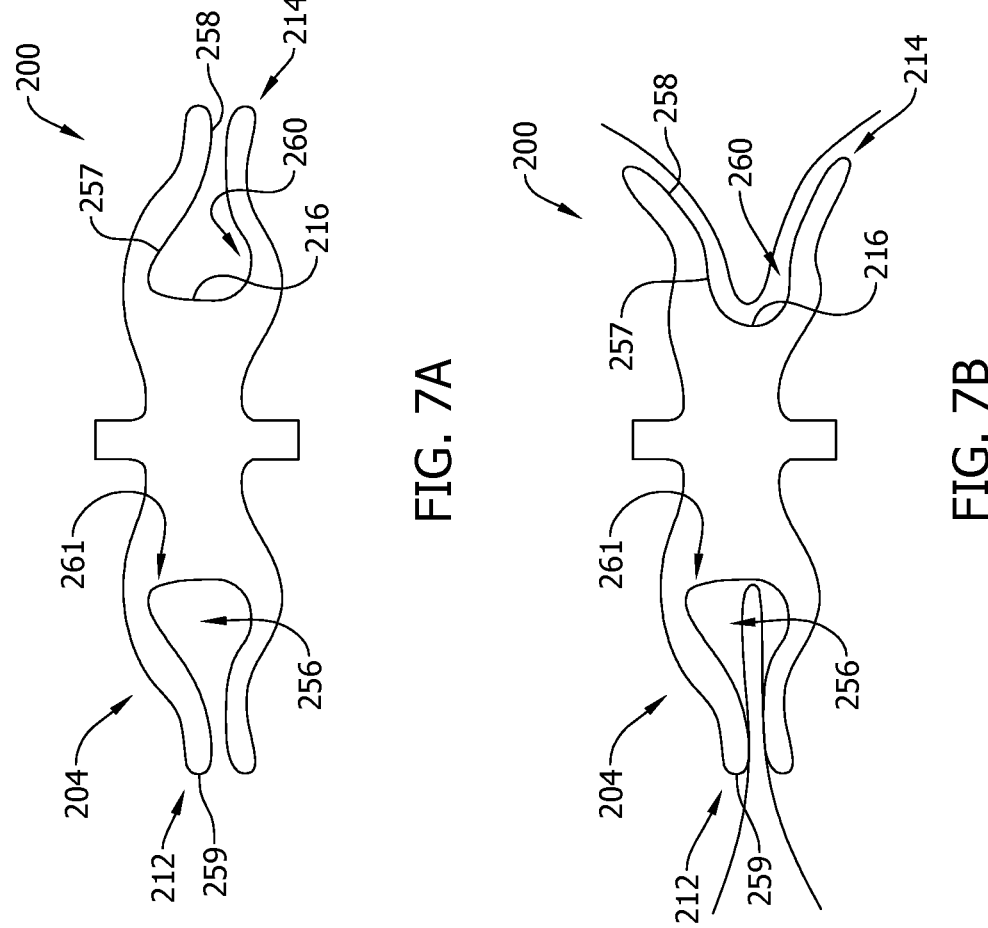
FIGS. 7A and 7B illustrate sectional side views of yet another exemplary embodiment of a medical device in accordance with the present disclosure, being deployed relative to example tissue.

One alternative embodiment of a medical device is shown in FIGS. 7A and 7B, referred to as medical device 200, in which only an outer layer 204 is shown for clarity. Medical device 200 may share any characteristics and features of medical device 100 disclosed herein. However, medical device 200 includes a distal disc 212 and a proximal disc 214 that differ in geometry from distal disc 112 and proximal disc 114. Specifically, distal disc 212 includes a proximal-facing concave tapered surface 256 having a concave portion 257 and a planar or flat portion 258 circumscribing the concave portion 257. Flat portion 258 connects to a peripheral surface 259. Concave portion 257 has a concavity facing proximal disc 214, or can be described as tapering radially outwardly. Stated differently, a distance between the tapered surface 256 and a distal-facing outer surface 260 of proximal disc 214 increases from an outer edge of distal disc 212 (e.g., as defined by peripheral surface 259) to a distal interface 261 between distal disc 212 and a device waist 216. Proximal disc 214 includes similar, but mirrored, geometry. This device geometry may facilitate improved conformance to and/or sealing against a tissue defect with a thinner profile.

As depicted in FIG. 2, a diameter of inner distal disc 112I is significantly smaller than a diameter of outer distal disc 112O. As used herein, with respect to the inner and outer layers of distal disc 112, "significantly smaller" refers to a distinct difference in the shapes and sizes of the inner and outer layers of distal disc 112. That is, inner distal disc 112I is not merely incidentally smaller than outer distal disc 112O solely because inner distal disc 112I is within outer distal disc 112O. Rather, inner layer 102 is significantly smaller than outer layer 104 at distal disc 112 and is selectively formed such that inner distal disc 112I is independent from outer distal disc 112O.

Figure 5:
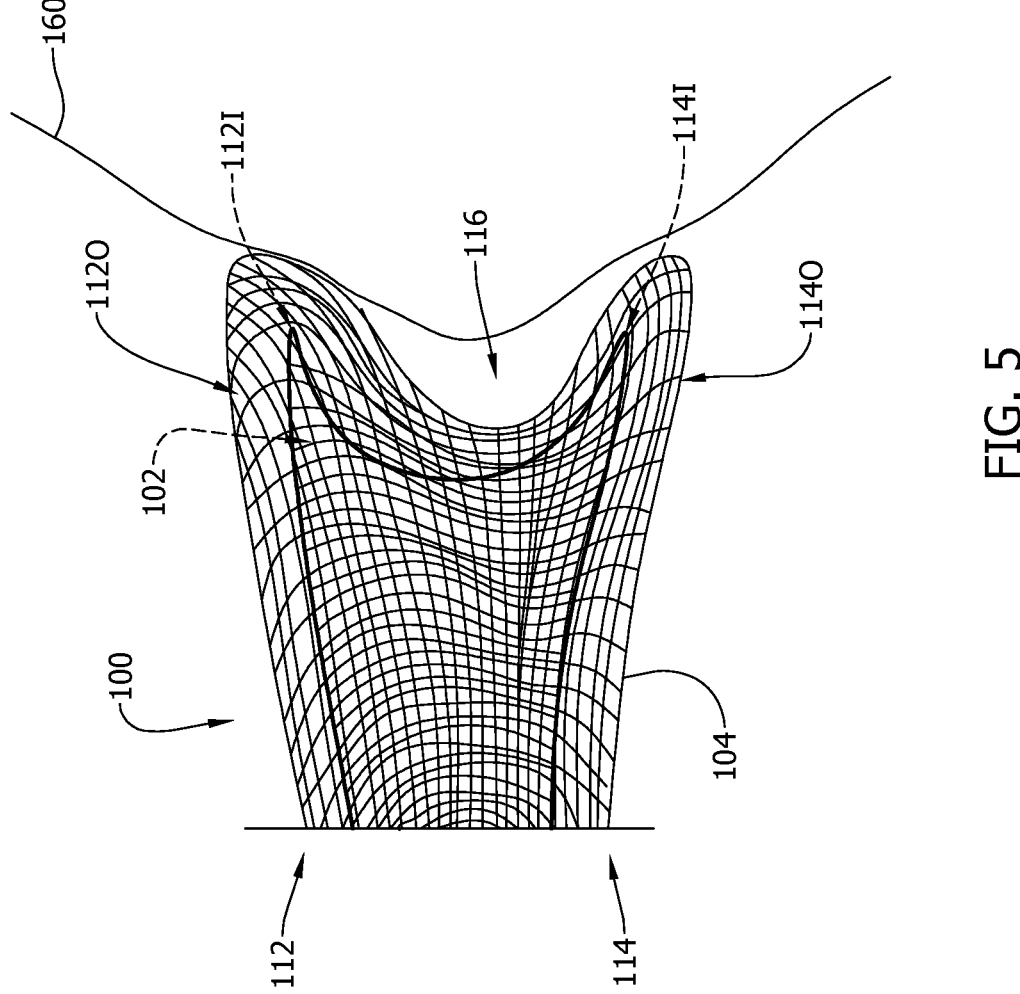
FIG. 5 illustrates a side cross-sectional view of an exemplary embodiment of a medical device in accordance with the present disclosure, in a deployed configuration relative to example tissue.

In particular, inner distal disc 112I is significantly smaller than outer distal disc 112O to ensure that the stability of distal disc 112 is maintained during and after deployment of medical device 100, without substantially affecting the flexibility of outer distal disc 112O (see, for example, FIG. 5). In various embodiments, however, the diameter of inner distal disc 112I may be selected, relative to the diameter of outer distal disc 112O, such that inner distal disc 112I reliably expands within outer distal disc 112O during deployment of medical device 100. In some embodiments, inner distal disc 112I radially extends—to inner peripheral surface 122I at the outer circumference thereof—a distance that is about halfway between an outer circumference of waist 116 and an outer circumference of outer distal disc 112O, which optimizes expansion of inner distal disc 112I without substantially impacting the conformability and flexibility of outer peripheral surface 142O (see FIGS. 3-5). In some specific embodiments, outer distal disc 112O has a circumference or outer diameter that extends radially about 6 millimeters (mm) to 8 mm beyond the circumference or outer diameter of waist 116, and inner distal disc 112I has a diameter that extends about 1 mm to 6 mm beyond the diameter of waist 116.

It has been realized that this significant difference in diameter between inner distal disc 112I and outer distal disc 112O, with inner distal disc 112I having an enhanced stiffness (compared to a softer, single-layer device), also increases a clamping force imparted by medical device 100 on the surrounding tissue.

Similarly, in at least some embodiments, inner proximal disc 114I is significantly smaller than outer proximal disc 114O (e.g., inner proximal disc 114I has a diameter that is significantly smaller than a diameter of outer proximal disc 114O), and proximal disc 114 may exhibit similar characteristics as described above relative to distal disc 112. In at least some embodiments, proximal disc 114 is substantially similar to distal disc 112 in many or all respects discussed herein. In some embodiments, proximal disc 114 may have a smaller overall profile than distal disc 112 of the same medical device 100, but may still exhibit similar characteristics (e.g., an inner proximal disc 114I with a substantially smaller diameter than an outer proximal disc 114O).

Inner layer 102 has a specifically selected and designed shape and size optimized for radial strength and stiffness, while minimizing a delivery profile of inner layer 102. Outer layer 104 is formed such that outer distal disc 112O is independent from inner distal disc 112I. Outer layer 104 has a specifically selected and designed shape and size optimized for softness and conformability, and flexibility of outer distal disc 112O relative to waist 116.

In one example embodiment, inner waist 116I has a diameter that is the same as or generally corresponds to a diameter of outer waist 116O. Stated differently, inner waist 116I is flush with or contacts outer waist 116O when medical device 100 is deployed. In such embodiments, waist 116 may generally exhibit the overall characteristics of each of inner waist 116I and outer waist 116O combined (e.g., a generally softer outer surface (which may be of the outer waist 116O) but a stiffness or strength defined by inner waist 116I). It is contemplated that, in alternative embodiments, the diameter of inner waist 116I may be significantly smaller than the diameter of outer waist 116O. Additionally, in the example embodiment, the length of inner waist 116I is the same as or generally corresponds to the length of outer waist 116O.

It has been realized that the shape and size of inner and outer layers 102, 104, specifically with respect to distal disc 112 and waist 116, can be selectively optimized based upon the particular anatomy of the target site. For example, the length of waist 116 can be optimized based upon a length (not shown) of the tissue defect at the target site. The length may be selected to be long enough such that a distance between distal disc 112 and proximal disc 114 can accommodate the atrial tissue, but short enough to reduce or eliminate gaps between discs and the tissue (between each of the distal and proximal discs 112, 114 and the tissue). The overall length of waist 116, in some example embodiments, is between about 1 mm and about 4 mm.

As another example, the tapered profile of outer proximal surface 144O of outer distal disc 112O may be optimized based upon the anatomy of the tissue defect. More specifically, a distal disc, such as distal disc 112 shown in FIG. 6 having outer proximal surface 144O tapered towards waist 116 of the device may enhance sealing contact between the medical device 100 and the tissue defect. Alternatively, a distal disc, such as distal disc 212 shown in FIGS. 7A and 7B, having a concave proximal surface (e.g., a proximal surface tapered away from the waist) may enhance conformability of the disc relative to the tissue defect and/or the clamping force provided by the disc while accommodating thinner tissue.

In the example embodiment, inner layer 102 and outer layer 104 are formed with inner distal interface 126I and outer distal interface 146O, respectively, to optimize the desired characteristics of inner layer 102 and outer layer 104. For example, in some embodiments, outer layer 104 includes a transition in pic rate (generally "pic transition") between outer proximal surface 144O and outer waist 116O, or along or adjacent to outer waist 116O. The pic rate (i.e., pics per inch, or PPI) of braided material generally describes the number of braid wire crossings per inch of material, in which a pic (sometimes also referred to as a 'pick') is a single crossing of braid wires. In the example embodiment, inner layer 102 is formed from a first braided self-expanding material 162 and outer layer 104 is formed from a second braided self-expanding material 164. The pic transition in outer layer 104 increases a braid density and/or reduces a helix length of the second braided self-expanding material 164 of outer layer 104 at outer waist 116O and/or, in some embodiments, near distal interface 146O.

It has been discerned in the conception of the present disclosure that such a pic transition may facilitate advantages over at least some known designs of an ASD occluder. For example, the pic transition facilitates improved expansion of distal disc 112, closer to its final diameter, more reliably and earlier in the deployment sequence. The pic transition in outer layer 104, combined with the flat or slightly tapered profile of outer proximal surface 144O of outer distal disc 112O, facilitates improved seating of distal disc 112 within the atrial tissue when medical device 100 is being deployed, and after medical device 100 is fully deployed. With reference to FIG. 4, it is shown that the tapered profile of outer proximal surface 144O of outer distal disc 112O enables waist 116 (e.g., outer waist 116O and/or inner waist 116I) to seat further into the defect before the outer edge of distal disc 112 (e.g., outer peripheral surface 142O) contacts an outer tissue 160 of the defect, near the aorta. This advantage may be further notable when deploying medical device 100 "off-axis" (e.g., a deployment of medical device 100 in which distal disc 112 is oriented at an angle from central longitudinal axis 110, as seen in FIG. 4), which is often the case, and may reduce the potential for distal disc 112 to prolapse, or be pulled axially through the tissue defect, while proximal disc 114 is being deployed in the right atrium.

Moreover, the pic transition in outer layer 104, along or adjacent to waist 116 (specifically, outer waist 116O), facilitates increased elongation of the second braided self-expanding material 164 forming outer waist 116O. This increased elongation may be advantageous when deploying medical device 100, as it improves conformability of outer layer 104 to the atrial tissue near the aorta, thereby further decreasing the potential for distal disc 112 to prolapse during and after deployment of medical device 100. In addition, the increased elongation facilitates medical device 100 accommodating thicker defects (e.g., an ASD formed in thicker septal tissue or thicker areas of the septum). With reference to FIG. 3, it is shown that the pic transition of outer layer 104 results in an increased braid density near waist 116. The increased elongation may be facilitated by the pic transition in outer layer 104, along or adjacent to waist 116 (specifically, outer waist 116O).

The pic transition may further facilitate improved radial expansion of waist 116 during deployment of medical device 100, which encourages the distal disc 112 to expand further towards its final expanded configuration, providing the advantages in deployment and seating described above. With reference to FIG. 3, the increased braid density near waist 116 resulting from the pic transition of outer layer 104 may facilitate increasing the diameter of distal disc 112 when deployed from waist 116, thereby reducing the potential for distal disc 112 to be pulled axially through the tissue defect.

The pic rate of the braided material may further define the helix length of the braided layer along the length of the medical device 100. As used herein, "longer" and "shorter" helix lengths refer to relative axial distance covered by a single revolution of a helical wire. By way of example, a wire having a "longer" helix length will extend a greater axial distance per helical revolution and have a greater helical pitch than a wire having a "shorter" helix length. It is further realized that a reduced helix length imparted by a pic transition in outer layer 104 may reduce cyclical strain and, thereby, fatigue, on medical device 100.

In some embodiments, inner layer 102 may include a pic transition adjacent to or along inner waist 116I, and may therefore include one or more of the advantageous features described above with respect to outer layer 104.

As described herein, inner layer 102 and outer layer 104 include differentiating features that are not necessarily specific to one region of device body 101. In particular, the number of wires, the wire diameter, and/or the braid pattern of the first and second braided self-expanding materials 162, 164 may be specifically selected such that inner layer 102 and outer layer 104 are optimized to enhance different characteristics of medical device 100 overall. It has been determined in the conception of the present disclosure that it is advantageous to select the first braided self-expanding material 162 for forming inner layer 102 to have a number of wires, a wire diameter, and/or a braid pattern to optimize, or maximize, a radial strength or stiffness of inner layer 102 while reducing or minimizing an overall size or profile of inner layer 102. It has been further determined that it is advantageous to select the second braided self-expanding material 164 for forming outer layer 104 to have a number of wires, a wire diameter, and/or a braid pattern to optimize, or maximize, a softness, contact area, conformability, and/or flexibility of outer layer 104.

Importantly, optimizing the inner and outer layers 102, 104 in such a way provides previously unrealized advantages over at least some known designs of an ASD occluder, including those advantages already discussed herein. Specifically, the improved softness of outer layer 104 reduces or eliminates tissue erosion around deployed medical device 100, by enhancing conformability of medical device 100 with surrounding tissue while reducing the frictional force imparted on the tissue by outer layer 104 (compared to, for example, single-layer occluders). However, a softer (single-layer) device may be more prone to extending or bulging into the atria as compressive and axial forces are applied to the waist and discs. Accordingly, the improved radial strength and stiffness provided to medical device 100 by inner layer 102 reduces or eliminates waist shrinkage or elongation and, thereby, reduces disc bulging of deployed medical device 100, without exacerbating tissue erosion (which may be experienced by a stiffer single-layer occluder). Reducing extension of the discs into the atria also facilitates reducing or eliminating leakage around waist 116 and reducing or eliminating undesirable blood flow characteristics around the distal and proximal discs 112, 114.

It has been realized, in accordance with the present disclosure, that the above-described benefits associated with the tapered shape of distal disc 112 are further enhanced by the above-described improved softness and conformability of outer layer 104. Specifically, the combination of these features has been determined to enable rounding of outer peripheral surface 142O while maintaining overall conformability of distal disc 112, collectively reducing trauma to surrounding tissue during and after deployment of medical device 100. With reference to FIG. 5, it is shown that the softer, more conformable outer layer 104 provides a rounded atraumatic shape as it conforms to the outer tissue 160, while the medical device 100 retains the benefits of the flat or tapered disc shape of the inner layer 102 that would have provided a more traumatic edge directed at the outer tissue 160.

The improved softness and conformability of outer layer 104 allows for optimized gap spacing between the proximal and distal discs 112, 114, dependent on the shape and profile of the surrounding anatomy (e.g., outer tissue 160), as shown in FIG. 5. A device with a gap between the proximal and distal discs that is too large could result in pockets for thrombus formation and reduced occlusion efficacy. Alternatively, a device with a gap between the proximal and distal discs that is too small could result in bulging of the discs, reduced occlusion for thicker areas of the septum, and/or reduced conformability around the adjacent anatomy.

In some embodiments, therefore, to realize these advantages, outer layer 104 may be formed from a material having more wires and/or smaller or thinner wires than inner layer 102. In one specific embodiment, outer layer 104 is formed from a material having 144 braided wires, and inner layer 102 is formed from a material having 36 braided wires. In other embodiments, outer layer 104 may be formed from a material having 288, 144, or 72 wires, for example, while inner layer is formed from a material having 72, 36, or fewer wires. In the example embodiment, inner layer 102 is formed from a first braided self-expanding material 162 and outer layer 104 is formed from a second braided self-expanding material 164. In the example embodiment, therefore, to realize the advantages, the second braided self-expanding material 164 of outer layer 104 may be formed with an increased number of wires and/or smaller or thinner wires than first braided self-expanding material 162 of inner layer 102. In one specific embodiment, second braided self-expanding material 164 of outer layer 104 is formed with 144 braided wires, and first braided self-expanding material 162 of inner layer 102 is formed with 36 braided wires. In other embodiments, second braided self-expanding material 164 of outer layer 104 may be formed with 288, 144, or 72 wires, for example, while first braided self-expanding material 162 of inner layer may be formed with 72, 36, or fewer wires. Materials with other numbers of wires are contemplated within the scope of the present disclosure.

Increasing the number of wires in the outer layer 104 (or, more particularly, in the second braided self-expanding material 164 of outer layer 104), compared to previous single-layer devices and compared to the inner layer 102 (or, more particularly, to the first braided self-expanding material 162 of inner layer 102), increases the surface area of contact between the outer layer 104 and the surrounding tissue, distributing the force exerted by medical device 100 over a larger surface area and, thereby, reducing pressure on the tissue. The selected, or increased, number of wires in the outer layer 104 (or in the second braided self-expanding material 164 of outer layer 104) also reduces the likelihood of device deformation (e.g., "cobra deformations") during deployment of medical device 100. Conversely, reducing the number of wires in (first braided self-expanding material 162 of) inner layer 102, compared to previous single-layer devices and compared to (second braided self-expanding material 164 of) outer layer 104, facilitates reducing the overall profile of medical device 100 while enhancing the stability, radial strength, and/or axial strength of inner layer 102. This improved stability reduces undesirable deformations of medical device 100 after deployment. Moreover, with reference to FIG. 3, during deployment, the increased number of wires in (second braided self-expanding material 164 of) outer layer 104, forming outer distal disc 112O, as well as the flattened shape of outer distal disc 112O, enables rounding of outer peripheral surface 142O during deployment of distal disc 112, which may improve device deliverability and reduce tissue trauma during device deployment.

Additionally, or alternatively, to enhance the softness of outer layer 104 and/or enhance the stability of inner layer 102, the outer layer 104 may be formed with thinner wires than the inner layer 102. In particular, to enhance the softness of outer layer 104 and/or enhance the stability of inner layer 102, second braided self-expanding material 164 of outer layer 104 may be formed with thinner wires than first braided self-expanding material 162 of inner layer 102. In one embodiment, for a 26 mm medical device 100, second braided self-expanding material 164 of outer layer 104 may be formed (e.g. from a material) with wires of a diameter of about 0.0035" or inches (in) to about 0.0045", and first braided self-expanding material 162 of inner layer 102 may be formed (e.g. from a material) with wires of about 0.006" to about 0.0065".

For medical device 100 of other sizes, different numbers of wires and/or wires with different braid diameters for the inner layer 102 and/or the outer layer 104 may be selected. In particular, different numbers of wires and/or wires with different braid diameters for the first braided self-expanding material 162 of inner layer 102 and/or second braided self-expanding material 164 of outer layer 104 may be selected. In general, suitable wire sizes for braids used to form braided occluders, such as medical device 100 of the present disclosure, of about 4 mm to about 40 mm, are in the range of about 0.0015" diameter to about 0.010" diameter wires (e.g., about 0.0015" to about 0.006" diameter wires for outer layer 104 and about 0.003" to about 0.010" diameter wires for inner layer 102).

In some embodiments, outer layer 104 (or, more particularly, the second braided self-expanding material 164 of outer layer 104) has a braid pattern that includes the pic transition described in detail above. In some embodiments, the inner layer 102 (or, more particularly, the first braided self-expanding material 162 of inner layer 102) is formed with a 1/1 braid pattern, to enhance the stability of inner layer 102 (e.g., to maintain structure and symmetry of inner layer 102 upon deployment (or forming and deployment) of medical device 100) without increasing the number of wires of the first braided self-expanding material 162.

The softness of the inner and outer layers of various structures of devices have been tested using the compression techniques described previously. The structures such as the outer distal disc 112O or outer proximal disc 114O of the device 100 that are softer than the corresponding inner distal disc 112I or inner proximal disc 114I typically require the application of a 0.1-0.3N force for 2 mm of compression. For comparison, relatively stiff single layer atrial septal occluder devices tested required the application of a 0.6-0.8N for a flat proximal disc and 0.4-0.5N for an angled distal disc for 2 mm of compression. The difference in measurement values obtained is attributed to the angled disc flexing about the waist of the device under compression. The softest single layer atrial septal occluder devices tested required the application of 0.5 N radial force for a flat proximal disc and 0.3N radial force for an angled distal disc for 2 mm of compression. For waist compression measurements, a radial force of 0.2N for 2 mm of compression was obtained for the softest devices and a radial force of 0.45N for 2 mm of compression was obtained for the stiffest devices. This range of 0.2N to 0.45N for 2 mm of compression may be desirable for a combined stiffness of the inner layer and outer layer of the waist of the device 100.

Turning back to FIGS. 1 and 2, in the exemplary embodiments, medical device 100 includes at least one occlusive patch 190 (see FIG. 2) positioned between inner layer 102 and outer layer 104. In one embodiment, occlusive patch 190 includes a distal occlusive patch 192 positioned between inner distal disc 112I and outer distal disc 112O and a proximal occlusive patch 194 positioned between inner proximal disc 114I and outer proximal disc 114O. Distal occlusive patch 192 extends radially outwardly to outer peripheral surface 142O and, in some embodiments, may curve axially to wrap around inner distal disc 112I. Likewise, where proximal occlusive patch 194 is present, proximal occlusive patch 194 extends radially to outer peripheral surface 150O and, in some embodiments, may curve axially to wrap around inner proximal disc 114I. In other embodiments, occlusive patch 190 may be positioned elsewhere and/or medical device 100 may include additional occlusive patch(es) 190 (e.g., an occlusive patch 190 within waist 116), without departing from the scope of the present disclosure.

It has been realized in the conception of the present disclosure that forming medical device 100 including occlusive patch 190 requires occlusive patch 190 to be split or cut prior to being positioned between inner layer 102 and outer layer 104. More specifically, each occlusive patch 190 is cut from a perimeter thereof to a center thereof, and thereafter the occlusive patch 190 is placed between the inner and outer layers 102, 104 in its respective position. Each occlusive patch 190 is then sealed, via suture, heat-sealing, adhesive, or the like, to ensure the occlusive patch 190 provides the desired occlusive effect. Each occlusive patch 190 is further attached to inner layer 102 and/or outer layer 104, via suture(s), stitch(es), adhesive, welding, or the like. FIG. 1 depicts exemplary sutures 196 coupling occlusive patch(es) 190 to device body 101 of medical device 100. It is further contemplated that additional patch material, filler, or other occlusive material may be positioned within device body 101 (e.g., between inner layer 102 and outer layer 104, or within inner layer 102) to enhance the occlusive effect of medical device 100.

In any of the embodiments described herein, inner layer 102 and outer layer 104 may be formed from a shape-memory material. In any of the embodiments described herein, first braided self-expanding material 162 of inner layer 102 and second braided self-expanding material 164 of outer layer 104 may be formed from a shape-memory material. One particular shape memory material that may be used is Nitinol. Nitinol alloys are highly elastic and are said to be "superelastic," or "pseudoelastic." This elasticity may allow the medical device 100 to be resilient and return to a preset, expanded configuration for deployment following passage in a distorted form (e.g., through a delivery catheter). It is also understood that first braided self-expanding material 162 of inner layer 102 and/or second braided self-expanding material 164 of outer layer 104 may be formed from various materials other than Nitinol that have elastic properties, such as stainless steel, trade named alloys such as Elgiloy®, or Hastalloy, Phynox®, MP35N, CoCrMo alloys, metal, polymers, or a mixture of metal(s) and polymer(s). Suitable polymers may include PET (Dacron™), polyester, polypropylene, polyethylene, HDPE, Pebax, nylon, polyurethane, silicone, PTFE, polyolefins and ePTFE. Additionally, it is contemplated that the inner layer (e.g. first braided self-expanding material 162 of inner layer 102) and/or the outer layer 104 (e.g. second braided self-expanding material 164 of outer layer 104) of medical device 100 may comprise any material that has the desired elastic properties to ensure that the device may be deployed and function as an occluder in a manner disclosed within this application.

In at least one exemplary embodiment, the material(s) forming inner layer 102 and outer layer 104 are heat-set or "pre-baked" on respective first and second mandrels. Thereafter, the first or inner material is enclosed within the second or outer material. The distal ends of both braided materials are coupled together, and the proximal ends of both braided materials are coupled together (e.g., at respective hubs or radiopaque markers, via welding, etc.). For example, the first braided self-expanding material 162 of inner layer 102 is enclosed within the second braided self-expanding material 164 of outer layer 104. The distal ends of first braided self-expanding material 162 and second braided self-expanding material 164 are coupled together, and the proximal ends of first braided self-expanding material 162 and second braided self-expanding material 164 are coupled together (e.g., at respective hubs or radiopaque markers, via welding, etc.), such as at a distal hub 107 (shown in FIGS. 2 and 3). An endscrew or other delivery mechanism, such as at a proximal hub 109 (shown in FIGS. 1 and 2), may be coupled to the proximal end of the as-yet unformed device, to enable coupling of the device to a delivery system for deployment at the target site. Thereafter, the layered, braided materials (e.g., first braided self-expanding material 162 and second braided self-expanding material 164) are molded (heat-set) to form the inner and outer layers 102, 104, respectively, having the shape, size, and other characteristics described herein. Occlusive patches 190 are cut, positioned between inner layer 102 and outer layer 104, and sutured (or otherwise coupled) to device body 101.

Occlusive patch(es) 190 may be formed from an occlusive fabric, knit, or thin polymer material. The polymer may include, for example, Poly-L-lactic acid (PLLA), Poly(glycolic acid) (PGA), Copolyesters of poly(e-caprolactone) (PCL), Trimethylene carbonate (TMC), Poly(d-diozanone) (PPDO), PET (Dacron™), polyester, polypropylene, polyethylene, HDPE, Pebax, nylon, PTFE, polyolefins and ePTFE.

Figure 8:
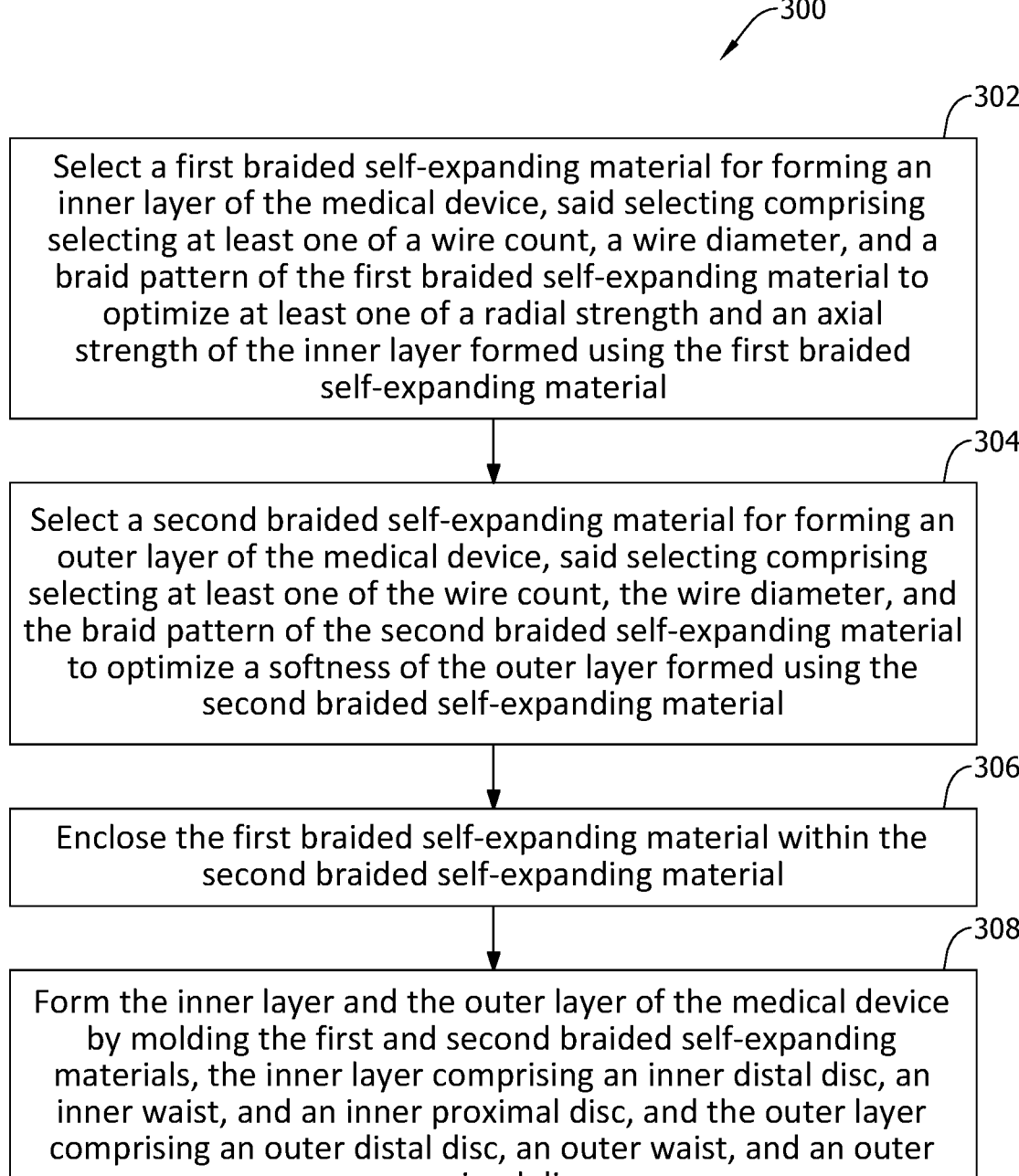
FIG. 8 is a flow diagram of an exemplary method of forming a medical device configured to close a tissue defect at a target site.

With reference to FIG. 8, a flow diagram of an exemplary method 300 of forming a medical device (e.g., medical device 100 and/or medical device 200, previously shown and described) that is configured to occlude an ASD in a patient is shown. In the exemplary embodiment, method 300 includes selecting 302 a first braided self-expanding material for forming an inner layer of the medical device. Selecting 302 includes selecting a wire count, a wire diameter, and/or a braid pattern of the first braided self-expanding material to optimize a radial strength of the inner layer formed using the first braided self-expanding material. Method 300 also includes selecting 304 a second braided self-expanding material for forming an outer layer of the medical device. Selecting 304 includes selecting the wire count, the wire diameter, and/or the braid pattern of the second braided self-expanding material to optimize a softness of the outer layer formed using the second braided self-expanding material.

Method 300 also includes enclosing 306 the first braided self-expanding material within the second braided self-expanding material, and forming 308 the inner layer and the outer layer of the medical device by molding (heat-setting) the first and second braided self-expanding materials. Once formed, the inner layer includes an inner distal disc, an inner waist, and an inner proximal disc, and the outer layer includes an outer distal disc, an outer waist, and an outer proximal disc.

Method 300 may include additional, alternative, and/or fewer steps, including those described herein. For example, in some embodiments, selecting 304 includes selecting a pic transition in the second braided self-expanding material at a location corresponding to the outer waist when the outer layer is formed from the second braided self-expanding material. In some embodiments, method 300 further includes positioning an occlusive patch material between the inner layer and the outer layer.

While embodiments of the present disclosure have been described, it should be understood that various changes, adaptations, and modifications may be made therein without departing from the spirit of the disclosure and the scope of the appended claims. Further, all directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. It is intended that all matter contained in the above description or shown in the accompanying drawings shall be interpreted as illustrative only and not limiting. Changes in detail or structure may be made without departing from the spirit of the disclosure as defined in the appended claims.

Many modifications and other embodiments of the disclosure set forth herein will come to mind to one skilled in the art to which this disclosure pertains having the benefit of the teachings presented in the foregoing descriptions and the associated drawings. Therefore, it is to be understood that the disclosure is not to be limited to the specific embodiments described and that modifications and other embodiments are intended to be included within the scope of the appended claims. Although specific terms are employed herein, they are used in a generic and descriptive sense only and not for purposes of limitation.

Any patent, publication, or other disclosure material, in whole or in part, that is said to be incorporated by reference herein is incorporated herein only to the extent that incorporated materials do not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A medical device for treating a target site, the medical device comprising:

a body extending from a proximal end to a distal end along a central longitudinal axis, the body comprising a proximal disc adjacent the proximal end, a distal disc adjacent the distal end, and a waist extending between and connecting the proximal disc and the distal disc, the body further comprising:

an inner layer formed from a first braided self-expanding material; and an outer layer formed from a second braided self-expanding material, wherein the outer layer surrounds the inner layer and is independent from the inner layer, wherein each of the proximal disc, the distal disc, and the waist are defined in part by each of the inner layer and the outer layer, wherein the distal disc includes an outer distal disc formed by the outer layer and an inner distal disc formed by the inner layer, and the waist includes an outer waist formed by the outer layer and an inner waist formed by the inner layer, the outer distal disc having an outer proximal surface, an outer distal surface, and an outer peripheral surface extending between the outer proximal surface and the outer distal surface, and the inner distal disc having an inner proximal surface, an inner distal surface and an inner peripheral surface extending between the inner proximal surface and the inner distal surface, in an expanded configuration of the medical device, the inner peripheral surface of the inner distal disc is positioned between the outer proximal surface and the outer distal surface of the outer distal disc and the inner waist contacts the outer waist, wherein, in the expanded configuration of the medical device, the outer proximal surface extends proximally and is tapered towards the outer waist such that a diameter of the outer proximal surface decreases gradually between an interface with the outer peripheral surface and an interface with the outer waist, wherein the outer layer comprises a pic transition at or near the interface between the outer proximal surface and the outer waist, such that (i) the pic transition in combination with the tapered outer proximal surface facilitates seating of the waist further into a defect at the target site before the outer peripheral surface contacts tissue at the defect and reduces the likelihood of prolapse of the distal disc during deployment, (ii) the pic transition improves the expansion of the distal disc during deployment of the medical device, and/or (iii) the pic transition facilitates increased elongation of the outer waist for improved deployability of the medical device and/or improved conformability of the outer layer to tissue at the target site, and wherein the first braided self-expanding material forming the inner layer comprises a first number of wires and the second braided self-expanding material forming the outer layer comprises a second number of wires greater than the first number of wires.

2. The medical device of claim 1, wherein, in the expanded configuration of the medical device, a diameter of the inner distal disc extends halfway between a diameter of the outer waist and a diameter of the outer distal disc.

3. The medical device of claim 1, wherein the outer distal disc, the inner distal disc, the outer waist and the inner waist each has a diameter, in the expanded configuration of the medical device, a diameter of the outer distal disc extends radially about 6 mm to 8 mm beyond a diameter of the outer waist, and a diameter of the inner distal disc extends about 1 mm to 6 mm beyond a diameter of inner waist.

4. The medical device of claim 1, wherein the inner layer has a first softness, and the outer layer has a second softness greater than the first softness.

5. The medical device of claim 4, wherein the first braided self-expanding material comprises the first number of wires having a first wire diameter, and the second braided self-expanding material comprises the second number of wires having a second wire diameter less than the first wire diameter.

6. The medical device of claim 5, wherein the second wire diameter is selected to optimize the second softness of the outer layer, and wherein the first wire diameter is selected to optimize at least one of a radial strength and an axial strength of the inner layer.

7. The medical device of claim 1, wherein the inner waist has a first radial strength, and the outer waist has a second radial strength less than the first radial strength.

8. The medical device of claim 1, wherein the pic transition comprises an increasing braid density of the second braided self-expanding material along or adjacent to the interface between the outer proximal surface and the outer waist.

9. The medical device of claim 1, wherein the pic transition comprises a decreasing helix length of the second braided self-expanding material along or adjacent to the interface between the outer proximal surface and the outer waist.

10. The medical device of claim 1, wherein the proximal disc includes an outer proximal disc formed by the outer layer and an inner proximal disc formed by the inner layer, the outer proximal disc having an outer distal surface and an outer proximal surface, in the expanded configuration of the medical device, the outer distal surface of the outer proximal disc being tapered toward the outer waist, such that a diameter of the outer distal surface of the outer proximal disc gradually decreases toward the outer waist.

11. The medical device of claim 1, wherein the pic transition results in an increased braid density of the outer layer at or near the outer waist.

12. The medical device of claim 1, wherein, in the expanded configuration of the medical device, a diameter of the inner waist is the same as a diameter of the outer waist.

13. The medical device of claim 1, further comprising an occlusive patch material positioned between the outer layer and the inner layer.

14. The medical device of claim 13, wherein the occlusive patch material is positioned within at least one of the distal disc and the proximal disc between the outer layer and the inner layer.

15. The medical device of claim 13, wherein the occlusive patch material is positioned within each of the distal disc, the proximal disc, and the waist between the outer layer and the inner layer.

16. The medical device of claim 1, wherein the proximal disc includes an outer proximal disc formed by the outer layer and an inner proximal disc formed by the inner layer, the outer proximal disc having an outer distal surface, an outer proximal surface, and an outer peripheral surface extending between the outer distal surface and the outer proximal surface, the outer peripheral surface of the outer proximal disc having a rounded profile.

17. A method of forming the medical device of claim 1, the method comprising:

selecting the first braided self-expanding material for forming the inner layer of the medical device, said selecting comprising selecting at least one of a wire count, a wire diameter, and a braid pattern of the first braided self-expanding material to optimize a radial strength of the inner layer formed using the first braided self-expanding material;

selecting the second braided self-expanding material for forming the outer layer of the medical device, said selecting comprising selecting at least one of a wire count, a wire diameter, and a braid pattern of the second braided self-expanding material to optimize a softness of the outer layer formed using the second braided self-expanding material;

enclosing the first braided self-expanding material within the second braided self-expanding material; and forming the inner layer and the outer layer of the medical device by molding the first and second braided self-expanding materials, the inner layer comprising the inner distal disc, the inner waist, and an inner proximal disc, and the outer layer comprising the outer distal disc, the outer waist, and an outer proximal disc.

18. The method of claim 17, wherein said forming the inner layer and the outer layer of the medical device comprises forming the inner distal disc to be significantly smaller than the outer distal disc.

19. The method of claim 17, further comprising:

positioning an occlusive patch material between the inner layer and the outer layer; and coupling the occlusive patch material to at least one of the inner layer and the outer layer.

20. The method of claim 17, wherein said selecting the second braided self-expanding material comprises selecting a pic transition at a location along or adjacent to the outer waist when the outer layer is formed using the second braided self-expanding material.

* * * * *